United States Patent
Gori et al.

(10) Patent No.: US 10,005,988 B2
(45) Date of Patent: Jun. 26, 2018

(54) REDUCING ADHESION OF BACTERIA TO A SURFACE OR RELEASING BACTERIA FROM A SURFACE TO WHICH THEY ADHERE USING ENDO-BETA-A,4-GLUCANASES

(71) Applicant: Novozymes A/S, Bagsvaerd (DK)

(72) Inventors: Klaus Gori, Copenhagen (DK); Lillian Eva Tang Baltsen, Bagsvaerd (DK); Marie Allesen-Holm, Hilleroed (DK)

(73) Assignee: NOVOZYMES A/S, Bagsvaerd (DK)

( * ) Notice: Subject to any disclaimer, the term of this patent is extended or adjusted under 35 U.S.C. 154(b) by 80 days.

(21) Appl. No.: 14/433,131

(22) PCT Filed: Oct. 3, 2013

(86) PCT No.: PCT/EP2013/070618
§ 371 (c)(1),
(2) Date: Apr. 2, 2015

(87) PCT Pub. No.: WO2014/053594
PCT Pub. Date: Apr. 10, 2014

(65) Prior Publication Data
US 2015/0252309 A1 Sep. 10, 2015

Related U.S. Application Data

(60) Provisional application No. 61/711,470, filed on Oct. 9, 2012.

(30) Foreign Application Priority Data

Oct. 5, 2012 (EP) ..................................... 12187547

(51) Int. Cl.
C11D 3/386 (2006.01)
C12N 9/42 (2006.01)
C11D 3/48 (2006.01)

(52) U.S. Cl.
CPC ...... *C11D 3/38636* (2013.01); *C11D 3/38645* (2013.01); *C11D 3/48* (2013.01); *C12N 9/2437* (2013.01); *C12Y 302/01004* (2013.01)

(58) Field of Classification Search
None
See application file for complete search history.

(56) References Cited

U.S. PATENT DOCUMENTS 5,356,803 A 10/1994 Carpenter et al.
2005/0112749 A1* 5/2005 Outtrup ................ C11D 3/386
435/200

FOREIGN PATENT DOCUMENTS

| EP | 2157162 A1 | 2/2010 |
| KR | 2012-0083605 A | 7/2012 |
| WO | 2004/053039 A2 | 6/2004 |
| WO | 2008/007318 A2 | 1/2008 |
| WO | 2008/007320 A2 | 1/2008 |
| WO | 2009/148800 A1 | 12/2009 |
| WO | 2010/069742 A1 | 6/2010 |

OTHER PUBLICATIONS

Novozymes, Inc 2008; "A new alternative to bleach".*
Leroy et al, 2008, Biofouling 24(1), 11-22.

* cited by examiner

*Primary Examiner* — Sheridan Swope
(74) *Attorney, Agent, or Firm* — Todd Sladek

(57) ABSTRACT

The present invention provides a method for reducing adhesion of bacteria to a surface, or releasing the bacteria from a surface to which they adhere, using an endo-beta-1,4-glucanase.

10 Claims, No Drawings

REDUCING ADHESION OF BACTERIA TO A SURFACE OR RELEASING BACTERIA FROM A SURFACE TO WHICH THEY ADHERE USING ENDO-BETA-A,4-GLUCANASES

CROSS-REFERENCE TO RELATED APPLICATIONS

This application is a 35 U.S.C. 371 national application of PCT/EP2013/070618 filed Oct. 3, 2013, which claims priority or the benefit under 35 U.S.C. 119 of European application no. 12187547.0 filed Oct. 5, 2012 and U.S. provisional application No. 61/711,470 filed Oct. 9, 2012. The content of each application is fully incorporated herein by reference.

REFERENCE TO A SEQUENCE LISTING

This application contains a Sequence Listing in computer readable form. The computer readable form is incorporated herein by reference.

FIELD OF THE INVENTION

The invention relates to methods for reducing adhesion of bacteria to a surface, or releasing the bacteria from a surface to which they adhere, using an endo-beta-1,4-glucanase.

BACKGROUND

When laundry items like T-shirts or sportswear are used, they are exposed to bacteria from the body of the user and from the rest of the environment in which they are used.

These bacteria are a source of bad odor, which develops after use, but which may remain even after wash. The reason for this bad odor is adhesion of bacteria to the textile surface. Because of the adhesion to the textile, the bacteria may remain even after wash, and thereby continue to be a source of bad odor.

The present invention provides a solution to this problem by reducing the adhesion of bacteria to the textile surface during wash. The selected bacteria are sources of very bad odor, and they were isolated from real-life laundry items.

SUMMARY

In a first aspect, the present invention provides a method for reducing adhesion of bacteria to a surface, or releasing the bacteria from a surface to which they adhere, comprising contacting the bacteria with an aqueous composition comprising an endo-beta-1,4-glucanase.

In another aspect, the present invention provides a method for reducing adhesion of bacteria selected from the group consisting of Brevundimonas sp., Exiguobacterium sp., Sphingobium sp., and Sphingomonas sp. to a surface, or releasing the bacteria from a surface to which they adhere, comprising contacting the bacteria with an aqueous composition comprising an endo-beta-1,4-glucanase.

In another aspect, the present invention provides a method for reducing adhesion of bacteria to a surface, or releasing the bacteria from a surface to which they adhere, comprising contacting the bacteria with an aqueous composition comprising an endo-beta-1,4-glucanase, wherein the aqueous composition comprises at least 1 mg/l of an endo-beta-1,4-glucanase.

In another aspect, the present invention provides a method for reducing adhesion of bacteria to a surface, or releasing the bacteria from a surface to which they adhere, comprising contacting the bacteria with an aqueous composition comprising an endo-beta-1,4-glucanase, wherein the amino acid sequence of the endo-beta-1,4-glucanase has at least 80% identity, preferably at least 90% identity, more preferably at least 95% identity, and most preferably 100% identity to the amino acid sequence of SEQ ID NO: 1.

In another aspect, the present invention provides a method for reducing adhesion of bacteria to a surface, or releasing the bacteria from a surface to which they adhere, comprising contacting the bacteria with an aqueous composition comprising an endo-beta-1,4-glucanase, wherein the aqueous composition also comprises a surfactant.

In another aspect, the present invention provides a method for reducing adhesion of bacteria to a surface, or releasing the bacteria from a surface to which they adhere, comprising contacting the bacteria with an aqueous composition comprising an endo-beta-1,4-glucanase, wherein the surface is a textile surface and the aqueous composition is a laundry detergent composition.

In another aspect, the present invention provides a method for reducing adhesion of bacteria to a surface, or releasing the bacteria from a surface to which they adhere, comprising contacting the bacteria with an aqueous composition comprising an endo-beta-1,4-glucanase, wherein the bacteria are Brevundimonas sp.

In another aspect, the present invention provides a method for reducing adhesion of bacteria to a surface, or releasing the bacteria from a surface to which they adhere, comprising contacting the bacteria with an aqueous composition comprising an endo-beta-1,4-glucanase, wherein the adhesion is reduced by at least 50%, or at least 50% of the bacteria are released from the surface.

In another aspect, the present invention provides a laundry composition comprising water; textile items; bacteria selected from the group consisting of Brevundimonas sp., Exiguobacterium sp., Sphingobium sp., and Sphingomonas sp.; and an endo-beta-1,4-glucanase.

In another aspect, the present invention provides a laundry composition comprising water; textile items; bacteria selected from the group consisting of Brevundimonas sp., Exiguobacterium sp., Sphingobium sp., and Sphingomonas sp.; and an endo-beta-1,4-glucanase, wherein the composition comprises at least 1 mg/l of an endo-beta-1,4-glucanase.

In another aspect, the present invention describes the use of an endo-beta-1,4-glucanase for reducing adhesion of bacteria to a surface, or releasing the bacteria from a surface to which they adhere.

In another aspect, the present invention describes the use of an endo-beta-1,4-glucanase for reducing adhesion of bacteria to a surface, or releasing the bacteria from a surface to which they adhere, wherein the bacteria are selected from the group consisting of Brevundimonas sp., Exiguobacterium sp., Sphingobium sp., and Sphingomonas sp.

DETAILED DESCRIPTION

Endo-beta-1,4-glucanase

Any endo-beta-1,4-glucanase known in the art may be used.

A suitable endo-beta-1,4-glucanase according to the present invention includes the polypeptide shown as amino acids 1 to 773 of SEQ ID NO: 1, which is a mature endo-glucanase sequence with a calculated molecular weight of 86 kDa.

It is believed that positions 1 to about 340 of SEQ ID NO: 1 are the catalytically active domain of the endo-glucanase enzyme. It is also believed that positions from about 340 to about 540 are the cellulose binding domain of the endo-glucanase enzyme.

The endo-beta-1,4-glucanase enzyme may comprise the amino acid sequence shown as (i) amino acids 1 to 773 of SEQ ID NO: 1, or a fragment thereof that has endo-glucanase activity. A fragment of amino acids 1 to 773 of SEQ ID NO: 1 is a polypeptide, which has one or more amino acids deleted from the amino and/or carboxyl terminus of SEQ ID NO: 1.

The present invention also provides the use of endo-glucanase polypeptides that are substantially homologous to the polypeptide of (i) above and species homologs (paralogs or orthologs) thereof. The term "substantially homologous" is used herein to denote polypeptides being at least 80%, preferably at least 85%, more preferably at least 90%, more preferably at least 95%, even more preferably at least 96% identical, even more preferably at least 97% identical, even more preferably at least 98% identical, and most preferably at least 99% or more identical to the amino acid sequence of SEQ ID NO: 1, or a fragment thereof that has endo-glucanase activity, or its orthologs or paralogs.

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows: (Identical Residues×100)/(Length of Alignment−Total Number of Gaps in Alignment)

In another embodiment, the endo-beta-1,4-glucanase of SEQ ID NO: 1 may comprise a substitution, deletion, and/or insertion at one or more (e.g., several) positions. In an embodiment, the number of amino acid substitutions, deletions and/or insertions introduced into the mature polypeptide of SEQ ID NO: 1 is not more than 10, e.g., 1, 2, 3, 4, 5, 6, 7, 8 or 9. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for endo-beta-1,4-glucanase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The endo-glucanase enzyme used in the invention may, in addition to the enzyme core comprising the catalytically active domain, i.e. amino acids 1 to about 340 of SEQ ID NO: 1, also comprise a cellulose binding domain (CBD), the cellulose binding domain and the catalytically active domain being operably linked. The cellulose binding domain (CBD) may exist as an integral part of the encoded enzyme as described above and in the appended SEQ ID NO: 1, or be a CBD from another origin, introduced into the endo-glucanase thus creating an enzyme hybrid. In this context, the term "cellulose-binding domain" is intended to be understood as defined by Peter Tomme et al. "Cellulose-Binding Domains: Classification and Properties" in "Enzymatic Degradation of Insoluble Carbohydrates", John N. Saddler and Michael H. Penner (Eds.), ACS Symposium Series, No. 618, 1996. This definition classifies more than 120 cellulose-binding domains into 10 families (I-X), and demonstrates that CBDs are found in various enzymes such as cellulases (endo-glucanases), xylanases, mannanases, arabinofuranosi-dases, acetyl esterases and chitinases. CBDs have also been found in algae, e.g. the red alga *Porphyra purpurea* as a non-hydrolytic polysaccharide-binding protein, see Tomme et al., op. cit. However, most of the CBDs are from cellulases and xylanases, CBDs are found at the N and C termini of proteins or are internal. Enzyme hybrids are known in the art, see e.g. WO 90/00609 and WO 95/16782, and may be prepared by transforming into a host cell a DNA construct comprising at least a fragment of DNA encoding the cellulose-binding domain ligated, with or without a linker, to a DNA sequence encoding the endo-glucanase and growing the host cell to express the fused gene. Enzyme hybrids may be described by the following formula:

CBD-MR-X wherein CBD is the N-terminal or the C-terminal region of an amino acid sequence corresponding to at least the cellulose-binding domain; MR is the middle region (the linker), and may be a bond, or a short linking group preferably of from about 2 to about 100 carbon atoms, more preferably of from 2 to 40 carbon atoms; or is preferably from about 2 to about 100 amino acids, more preferably of from 2 to 40 amino acids; and X is an N-terminal or C-terminal region of a polypeptide corresponding at least to the catalytically active domain encoded by the DNA sequence of the invention.

In a similar way, the cellulose binding domain corresponding to amino acids 340 to 540 of SEQ ID NO: 1 can be used to form hybrids with endo-glucanases from sources. Examples of endo-glucanases from other sources replacing the endo-glucanase of amino acids 1 to 340 of SEQ ID NO: 1 include endo-glucanases from: (a) *Bacillus lautus*, for instance *Bacillus lautus* NCIMB 40250 disclosed in WO 91/10732, (b) *Humicola insolens* DSM1800 disclosed in WO 91/17243, (c) *Fusarium oxysporium* DSM2672 disclosed in WO 91/17243, and (d) *Bacillus* sp. AC13 NCIMB 40482 disclosed in EP 0651785.

The concentration of the endo-beta-1,4-glucanase is typically in the range of 0.01-100 ppm enzyme protein, preferably 0.05-50 ppm enzyme protein, more preferably 0.1-50 ppm enzyme protein, more preferably 0.1-30 ppm enzyme protein, more preferably 0.5-20 ppm enzyme protein, and most preferably 0.5-10 ppm enzyme protein.

In an embodiment, the concentration of the endo-beta-1, 4-glucanase is typically in the range of 1-40 ppm enzyme protein, preferably 1-20 ppm enzyme protein, more preferably 1-10 ppm enzyme protein.

Determination of endo-beta-1,4-glucanase Activity

ECU Method

In the ECU method, the ability of the enzyme sample to reduce the viscosity of a solution of carboxymethyl-cellulose (CMC) is determined, and the result is given in ECU. The reduction in viscosity is proportional to the endo-cellulase activity. Conditions: CMC type 7LFD from Hercules, pH 7.5 in 0.1M phosphate buffer, CMC concentration 31.1 g per liter reaction at 40° C. for 30 minutes. A vibration viscosimeter such as MIVI 3000, Sofraser, France is used to measure the viscosity.

Cellazyme C Method

Cellazyme C is an endo-glucanase assay substrate, supplied in tablet form by Megazyme International Ireland Ltd. Reference is made to Megazyme's pamphlet CZC 7/99 which states: "The substrate is prepared by dyeing and cross-linking HE-cellulose to produce a material which hydrates in water but is water insoluble. Hydrolysis by endo-beta-1,4-glucanase produces water-soluble dyed fragments, and the rate of release of these (increase in absorbance at 590 nm) can be related directly to enzyme activity."

The enzyme sample is added to 6 ml of a suitable buffer in a test tube, one Cellazyme C tablet is added and dispersed by shaking the tube, then the tube is placed in a water bath at 40° C. The contents are mixed by brief shaking after approximately 15, 30, 45 and 60 minutes. After 60 minutes the solution is filtered through Whatman GF/C filters, 9 cm diameter. The absorbance of the filtered solution is measured at 590 nm.

Detergent Composition

In one aspect of the invention, the endo-beta-1,4-glucanase is added to and thus becomes a component of a detergent composition.

The detergent composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art.

When included therein, the detergent will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein, the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamide (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

The detergent composition may contain about 0-65% by weight of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in laundry detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), iminodiethanol (DEA) and 2,2',2"-nitrilotriethanol (TEA), and carboxymethylinulin (CMI), and combinations thereof.

The detergent composition may contain 0-50% by weight of a bleaching system. Any bleaching system known in the art for use in laundry detergents may be utilized. Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. By Bleach activator is meant herein a compound which reacts with peroxygen bleach like hydrogen peroxide to form a Peracid. The peracid thus formed constitutes the activated bleach. Suitable bleach activators to be used herein include those belonging to the class of esters amides, imides or anhydrides, Suitable examples are tetracetyl athylene diamine (TAED), sodium 3,5,5 trimethyl hexanoyloxybenzene sulphonat, diperoxy dodecanoic acid, 4-(dodecanoyloxy)benzene-sulfonate (LOBS), 4-(decanoyloxy)benzenesulfonate, 4-(decanoyloxy)benzoate (DOBS), 4-(3,5,5-trimethylhexanoyloxy)benzenesulfonate (ISONOBS), tetraacetylethylenediamine (TAED) and 4-(nonanoyloxy)benzenesulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like Triacin has the advantage that it is environmental friendly as it eventually degrades into citric acid and alcohol. Furthermore, acethyl triethyl citrate and triacetin has a good hydrolytical stability in the product upon storage and it is an efficient bleach activator. Finally, ATC provides a good building capacity to the laundry additive. Alternatively, the bleaching system may comprise peroxyacids of, for example, the amide, imide, or sulfone type. The bleaching system may also comprise peracids such as 6-(phthaloylamino)-percapronic acid (PAP). The bleaching system may also include a bleach catalyst.

Other ingredients of the detergent composition, which are all well-known in art, include hydrotropes, fabric hueing agents, anti-foaming agents, soil release polymers, anti-redeposition agents etc.

The detergent additive as well as the detergent composition may comprise one or more additional enzymes such as a protease, lipase, cutinase, amylase, carbohydrase, cellulase, pectinase, mannanase, arabinase, galactanase, xylanase, oxidase, e.g., a laccase, and/or peroxidase.

The endo-beta-1,4-glucanase of the present invention may be added to a detergent composition in an amount corresponding to at least 1 mg of endo-beta-1,4-glucanase protein, such as at least 5 mg of protein, preferably at least 10 mg of protein, more preferably at least 15 mg of protein, even more preferably at least 20 mg of protein, most preferably at least 30 mg of protein, and even most preferably at least 40 mg of protein per liter of wash liquor. Thus, the detergent composition may comprise at least 0.1% endo-beta-1,4-glucanase protein, preferably at least 0.2%, 0.3%, 0.4%, 0.5%, 0.6%, 0.8%, 1.0%, 1.2%, 1.5%, or 2.0% of endo-beta-1,4-glucanase protein.

The polypeptide having endo-beta-1,4-glucanase activity may be formulated as a liquid (e.g. aqueous), a solid, a gel, a paste or a dry product formulation. The dry product formulation may subsequently be re-hydrated to form an active liquid or semi-liquid formulation usable in the methods of the invention.

The compositions of the invention may further comprise auxiliary agents such as wetting agents, thickening agents, buffer(s) for pH control, stabilisers, perfume, colourants, fillers and the like.

Useful wetting agents are surfactants, i.e. non-ionic, anionic, amphoteric or zwitterionic surfactants. Surfactants are further described above.

Methods and Uses

In a first aspect, the present invention provides a method for reducing adhesion of bacteria to a surface, or releasing the bacteria from a surface to which they adhere, comprising contacting the bacteria with an aqueous composition comprising an endo-beta-1,4-glucanase.

In an embodiment, the present invention provides a method for reducing adhesion of Gram-negative and/or Gram-positive bacteria to a surface, or releasing the bacteria from a surface to which they adhere, comprising contacting the bacteria with an aqueous composition comprising an endo-beta-1,4-glucanase.

In an embodiment, the present invention provides a method for reducing adhesion of bacteria selected from the group consisting of Brevundimonas sp., Exiguobacterium sp., Sphingobium sp., and Sphingomonas sp. to a surface, or releasing the bacteria from a surface to which they adhere, comprising contacting the bacteria with an aqueous composition comprising an endo-beta-1,4-glucanase.

Preferably, the aqueous composition comprises at least 1 mg/l of an endo-beta-1,4-glucanase. More preferably, the amino acid sequence of the endo-beta-1,4-glucanase has at least 80% identity, preferably at least 90% identity, more preferably at least 95% identity, and most preferably 100% identity to the amino acid sequence of SEQ ID NO: 1.

In an embodiment, the aqueous composition also comprises a surfactant; and optionally also a detergent builder or co-builder. Preferably, the surface is a textile surface and the aqueous composition is a laundry detergent composition. The textile surface may be the surface of any textile item, such as an item made of cotton or a synthetic material, for example a piece of sportswear, a T-shirt, or another piece of clothing which is exposed to sweat when used. The textile surface may also be the surface of bedding, bed linen or towels.

In an embodiment, the bacteria are Brevundimonas sp.

In an embodiment, the bacterial adhesion is reduced by at least 50%, or at least 50% of the bacteria are released from the surface.

In another aspect, the invention provides a detergent composition comprising at least 3% surfactant, and at least 0.1% of an endo-beta-1,4-glucanase.

In another aspect, the invention provides a (laundry) composition comprising water; textile items; bacteria selected from the group consisting of Brevundimonas sp., Exiguobacterium sp., Sphingobium sp., and Sphingomonas sp.; and an endo-beta-1,4-glucanase. Preferably, the composition comprises at least 1 mg/l of an endo-beta-1,4-glucanase. The textile item may be an item made of cotton or a synthetic material, for example a piece of sportswear, a T-shirt, or another piece of clothing which is exposed to sweat when used. The textile item may also be bedding, bed linen or towels.

The invention also provides for use of the methods and compositions above for reducing adhesion of bacteria selected from the group consisting of Brevundimonas sp., Exiguobacterium sp., Sphingobium sp., and Sphingomonas sp. to a surface, or releasing the bacteria from a surface to which they adhere.

The methods according to the invention may be carried out at a temperature between 0 and 70 degrees Celsius, preferably between 5 and 60 degrees Celsius, more preferably between 5 and 50 degrees Celsius, even more preferably between 5 and 40 degrees Celsius, even more preferably between 5 and 35 degrees Celsius, most preferably between 5 and 30 degrees Celsius, and in particular between 10 and 30 degrees Celsius.

The methods of the invention may employ a treatment time of from 5 minutes to 120 minutes, preferably from 5 minutes to 90 minutes, more preferably from 5 minutes to 60 minutes, more preferably from 5 minutes to 45 minutes, more preferably from 5 minutes to 30 minutes, most preferably from 5 minutes to 20 minutes, and in particular from 5 minutes to 15 minutes.

The methods of the invention may be carried out at pH 3 to pH 11, preferably at pH 5 to pH 10, more preferably at pH 7 to pH 9. Most preferably, the methods of the invention are carried out at the pH or temperature optimum of the endo-beta-1,4-glucanase+/−one pH unit.

The present invention is further described by the following examples which should not be construed as limiting the scope of the invention.

EXAMPLES

Chemicals used as buffers and substrates were commercial products of at least reagent grade. The endo-beta-1,4-glucanase (see also WO 02/099091) used in the following Example has an amino acid sequence shown as SEQ ID NO: 1.

Example 1

Reducing Adhesion of Bacteria to a Surface Using endo-beta-1,4-glucanase

One of the aims of the present study was to investigate the bacterial diversity in laundry after washing at 15, 40 and 60° C., respectively.

The study was conducted on laundry collected from Danish households. For each wash, 20 g of laundry items (tea towel, towel, dish cloth, bib, T-shirt armpit, T-shirt collar, socks) in the range 4:3:2:2:1:1:1 was used. Washing was performed in a Laundr-O-Meter (LOM) at 15, 40 and 60° C. For washing at 15 and 40° C., Ariel Sensitive White & Color was used, whereas WFK IEC-A* model detergent was used for washing at 60° C. Ariel Sensitive White & Color was prepared by weighing out 5.1 g and adding tap water up to 1000 ml followed by stirring for 5 minutes. WFK IEC-A* model detergent was prepared by weighing out 5 g and adding tap water up to 1300 ml followed by stirring for 15 min. Washing was performed for 1 hour at 15, 40 and 60° C., respectively, followed by 2 times rinsing for 20 min at 15° C.

Laundry was sampled immediately after washing at 15, 40 and 60° C., respectively. Twenty grams of laundry was added 0.9% (w/v) NaCl (1.06404; Merck, Damstadt, Germany) with 0.5% (w/w) Tween 80 to yield a 1:10 dilution in stomacher bag. The mixture was homogenized using a Stomacher for 2 minutes at medium speed. After homogenization, ten-fold dilutions were prepared in 0.9% (w/v) NaCl. Bacteria were enumerated on Tryptone Soya Agar (CM0129, Oxoid, Basingstoke, Hampshire, UK) incubated aerobically at 30° C. for 5-7 days. To suppress growth of yeast and moulds, 0.2% sorbic acid (359769, Sigma) and 0.1% cycloheximide (18079; Sigma) were added. Twenty-four bacterial and fungal colonies were selected from countable plates and purified by restreaking twice on Tryptone Soya Agar (TSA). For long time storage, purified isolates were stored at −80° C. in TSB containing 20% (w/v) glycerol (49779; Sigma).

Four strains of *Brevundimonas* sp., one strain of *Sphingomonas* sp., one strain of *Sphingobium* sp., and one strain of *Exiguobacterium* sp. (all isolated as described above) were used in the present study. For long term storage, bacterial strains were maintained at −80° C. in Tryptone Soya Broth (TSB) (pH 7.3) (CM0129, Oxoid Ltd, Basingstoke, UK), to which 20% (v/v) glycerol (Merck, Darmstadt, Germany) was added. Bacterial cultures were pre-grown on Tryptone Soya Agar (TSA) (pH 7.3) for 3-5 days at 30° C. From a single colony, a loop-full was transferred to a test tube containing 10 ml TSB and incubated for 1 day at 30° C. with shaking (240 rpm).

After incubation, the bacterial cells were diluted 1000 times in TSB added 0, 0.5, 1, 2, 4, 8, 16, 32, 64, 128 and 256 ppm of endo-beta-1,4-glucanase. One hundred µl was inoculated into a 96-well polystyrene plate (flat bottom) (161093; Nunc, Roskilde, Denmark) and incubated for 3 days at 30° C.

After incubation, growth was determined by measurement of the optical density, measured at 600 nm using a Spectramax Plus384 reader (Molecular Devices, Sunnyvale, Calif., USA).

Adhesion/biofilm prevention was measured by removing non-adherent cells by washing two times with 0.9% (w/v) NaCl (Merck). To measure adherence, 200 µl of 0.1% (w/v) crystal violet (C0775; Sigma-Aldrich, St. Louis, Mo., USA) was added and left for 15 minutes at room temperature. The wells were washed two times with 0.9% (w/v) NaCl, and bound crystal violet was eluted by the addition of 200 µl 96% (w/v) ethanol (201145; Kemetyl, Køge, Denmark) and determined by measurement at 595 nm.

TABLE 1

Inhibition dosages of the endo-beta-1,4-glucanase, which is the lowest dose at which prevention of adhesion/biofilm formation was observed.

| Bacterial strain | Inhibition dosage (mg/l) |
|---|---|
| *Brevundimonas* sp. 1 | 0.5 |
| *Brevundimonas* sp. 2 | 0.5 |
| *Brevundimonas* sp. 3 | 0.5 |
| *Brevundimonas* sp. 4 | 1 |
| *Exiguobacterium* sp. 1 | 1 |
| *Sphingobium* sp. 1 | 32 |
| *Sphingomonas* sp. 1 | 62 |

The study shows that endo-beta-1,4-glucanase decreases the adhesion properties of *Brevundimonas* sp., *Sphingobium* sp., *Sphingomonas* sp. and *Exiguobacterium* sp. found in washed laundry, where they may cause textile damage or produce malodor when the textiles are used again after being washed.

Most importantly, inhibition of adhesion properties will prevent transfer of these bacteria between different textile items during the washing process and thus limit the occurrence of these bacteria. Furthermore, inhibition of adhesion properties will minimize the risk of growth of these bacteria inside the washing machine. Growth of bacteria inside the washing machine may cause malodor from the washing machine. Furthermore, detached bacteria may be transferred to textiles during the washing process and later cause malodor from textiles when they are used after the washing process.

The invention claimed is:

1. A method for reducing adhesion of bacteria to a surface, or releasing the bacteria from a surface to which they adhere, comprising contacting the bacteria with an aqueous composition comprising sequence of SEQ ID NO: 1 with a protein comprising the endo-beta-1,4-glucanase consisting of the amino acid sequence of SEQ ID NO: 1.

2. The method according to claim 1, wherein the bacteria are selected from the group consisting of *Brevundimonas* sp., *Exiguobacterium* sp., *Sphingobium* sp., and *Sphingomonas* sp.

3. The method of claim 1, wherein the aqueous composition comprises at least 1 mg/l of the endo-beta-1,4-glucanase.

4. The method of claim 1, wherein the aqueous composition also comprises a surfactant.

5. The method of claim 1, wherein the surface is a textile surface and the aqueous composition is a laundry detergent composition.

6. The method of claim 1, wherein the bacteria are *Brevundimonas* sp.

7. The method of claim 1, wherein the adhesion is reduced by at least 50%, or at least 50% of the bacteria are released from the surface.

8. A method for releasing bacteria from a textile surface to which they adhere, comprising:
   contacting the bacteria with an aqueous composition comprising a protein comprising the endo-beta-1,4-glucanase consisting of the amino acid sequence of SEQ ID NO: 1 and has endo-glucanase activity.

9. The method of claim 8, wherein the bacteria are isolated from laundry items.

10. The method of claim 9, wherein the bacteria comprise one or more of a *Brevundimonas* sp., *Exiguobacterium* sp., *Sphingobium* sp., and *Sphingomonas* sp.

* * * * *

SEQUENCE LISTING

```
<160> NUMBER OF SEQ ID NOS: 1

<210> SEQ ID NO 1
<211> LENGTH: 773
<212> TYPE: PRT
<213> ORGANISM: Bacillus ap.

<400> SEQUENCE: 1

Ala Glu Gly Asn Thr Arg Glu Asp Asn Phe Lys His Leu Leu Gly Asn
1               5                   10                  15

Asp Asn Val Lys Arg Pro Ser Glu Ala Gly Ala Leu Gln Leu Gln Glu
            20                  25                  30

Val Asp Gly Gln Met Thr Leu Val Asp Gln His Gly Glu Lys Ile Gln
        35                  40                  45

Leu Arg Gly Met Ser Thr His Gly Leu Gln Trp Phe Pro Asp Ile Leu
    50                  55                  60

Asn Asp Asn Ala Tyr Lys Ala Leu Ala Asn Asp Trp Glu Ser Asn Met
65                  70                  75                  80

Ile Arg Leu Ala Met Tyr Val Gly Glu Asn Gly Tyr Ala Ser Asn Pro
                85                  90                  95

Glu Leu Ile Lys Ser Arg Val Ile Lys Gly Ile Asp Leu Ala Ile Glu
            100                 105                 110

Asn Asp Met Tyr Val Ile Val Asp Trp His Val His Ala Pro Gly Asp
        115                 120                 125

Pro Arg Asp Pro Val Tyr Ala Gly Ala Glu Asp Phe Phe Arg Asp Ile
    130                 135                 140

Ala Ala Leu Tyr Pro Asn Asn Pro His Ile Ile Tyr Glu Leu Ala Asn
145                 150                 155                 160
```

-continued

Glu Pro Ser Ser Asn Asn Asn Gly Gly Ala Gly Ile Pro Asn Asn Glu
                165                 170                 175

Glu Gly Trp Asn Ala Val Lys Glu Tyr Ala Asp Pro Ile Val Glu Met
            180                 185                 190

Leu Arg Asp Ser Gly Asn Ala Asp Asp Asn Ile Ile Ile Val Gly Ser
        195                 200                 205

Pro Asn Trp Ser Gln Arg Pro Asp Leu Ala Ala Asp Asn Pro Ile Asn
    210                 215                 220

Asp His His Thr Met Tyr Thr Val His Phe Tyr Thr Gly Ser His Ala
225                 230                 235                 240

Ala Ser Thr Glu Ser Tyr Pro Pro Glu Thr Pro Asn Ser Glu Arg Gly
                245                 250                 255

Asn Val Met Ser Asn Thr Arg Tyr Ala Leu Glu Asn Gly Val Ala Val
            260                 265                 270

Phe Ala Thr Glu Trp Gly Thr Ser Gln Ala Asn Gly Asp Gly Gly Pro
        275                 280                 285

Tyr Phe Asp Glu Ala Asp Val Trp Ile Glu Phe Leu Asn Glu Asn Asn
    290                 295                 300

Ile Ser Trp Ala Asn Trp Ser Leu Thr Asn Lys Asn Glu Val Ser Gly
305                 310                 315                 320

Ala Phe Thr Pro Phe Glu Leu Gly Lys Ser Asn Ala Thr Asn Leu Asp
                325                 330                 335

Pro Gly Pro Asp His Val Trp Ala Pro Glu Glu Leu Ser Leu Ser Gly
            340                 345                 350

Glu Tyr Val Arg Ala Arg Ile Lys Gly Val Asn Tyr Glu Pro Ile Asp
        355                 360                 365

Arg Thr Lys Tyr Thr Lys Val Leu Trp Asp Phe Asn Asp Gly Thr Lys
    370                 375                 380

Gln Gly Phe Gly Val Asn Ser Asp Ser Pro Asn Lys Glu Leu Ile Ala
385                 390                 395                 400

Val Asp Asn Glu Asn Asn Thr Leu Lys Val Ser Gly Leu Asp Val Ser
                405                 410                 415

Asn Asp Val Ser Asp Gly Asn Phe Trp Ala Asn Ala Arg Leu Ser Ala
            420                 425                 430

Asp Gly Trp Gly Lys Ser Val Asp Ile Leu Gly Ala Glu Lys Leu Thr
        435                 440                 445

Met Asp Val Ile Val Asp Glu Pro Thr Thr Val Ala Ile Ala Ala Ile
450                 455                 460

Pro Gln Ser Ser Lys Ser Gly Trp Ala Asn Pro Glu Arg Ala Val Arg
465                 470                 475                 480

Val Asn Ala Glu Asp Phe Val Gln Gln Thr Asp Gly Lys Tyr Lys Ala
                485                 490                 495

Gly Leu Thr Ile Thr Gly Glu Asp Ala Pro Asn Leu Lys Asn Ile Ala
            500                 505                 510

Phe His Glu Glu Asp Asn Asn Met Asn Asn Ile Ile Leu Phe Val Gly
        515                 520                 525

Thr Asp Ala Ala Asp Val Ile Tyr Leu Asp Asn Ile Lys Val Ile Gly
    530                 535                 540

Thr Glu Val Glu Ile Pro Val Val His Asp Pro Lys Gly Glu Ala Val
545                 550                 555                 560

Leu Pro Ser Val Phe Glu Asp Gly Thr Arg Gln Gly Trp Asp Trp Ala
                565                 570                 575

-continued

```
Gly Glu Ser Gly Val Lys Thr Ala Leu Thr Ile Glu Glu Ala Asn Gly
            580                 585                 590

Ser Asn Ala Leu Ser Trp Glu Phe Gly Tyr Pro Glu Val Lys Pro Ser
        595                 600                 605

Asp Asn Trp Ala Thr Ala Pro Arg Leu Asp Phe Trp Lys Ser Asp Leu
        610                 615                 620

Val Arg Gly Glu Asn Asp Tyr Val Ala Phe Asp Phe Tyr Leu Asp Pro
625                 630                 635                 640

Val Arg Ala Thr Glu Gly Ala Met Asn Ile Asn Leu Val Phe Gln Pro
                645                 650                 655

Pro Thr Asn Gly Tyr Trp Val Gln Ala Pro Lys Thr Tyr Thr Ile Asn
            660                 665                 670

Phe Asp Glu Leu Glu Glu Ala Asn Gln Val Asn Gly Leu Tyr His Tyr
        675                 680                 685

Glu Val Lys Ile Asn Val Arg Asp Ile Thr Asn Ile Gln Asp Asp Thr
        690                 695                 700

Leu Leu Arg Asn Met Met Ile Ile Phe Ala Asp Val Glu Ser Asp Phe
705                 710                 715                 720

Ala Gly Arg Val Phe Val Asp Asn Val Arg Phe Glu Gly Ala Ala Thr
                725                 730                 735

Thr Glu Pro Val Glu Pro Glu Pro Val Asp Pro Gly Glu Glu Thr Pro
            740                 745                 750

Pro Val Asp Glu Lys Glu Ala Lys Lys Glu Gln Lys Glu Ala Glu Lys
        755                 760                 765

Glu Glu Lys Glu Glu
        770
```